United States Patent [19]
Kakimoto et al.

[11] Patent Number: 4,849,236
[45] Date of Patent: Jul. 18, 1989

[54] METHOD FOR MAINTAINING FRESHNESS OF VEGETABLES BY INCREASING GERMANIUM CONTENT

[75] Inventors: Norihiro Kakimoto, Machida; Teizou Sakai, Osaka; Yoshinori Sasaki, Tokyo, all of Japan

[73] Assignees: Kabushikikaisha Germax, Tokyo; Naigai Foods Kabushikikaisha, Osaka, both of Japan

[21] Appl. No.: 2,659

[22] PCT Filed: Mar. 14, 1986

[86] PCT No.: PCT/JP86/00130
§ 371 Date: Nov. 14, 1986
§ 102(e) Date: Nov. 14, 1986

[87] PCT Pub. No.: WO86/05354
PCT Pub. Date: Sep. 25, 1986

[30] Foreign Application Priority Data
Mar. 14, 1985 [JP] Japan ................... 60-49290
Jun. 20, 1985 [JP] Japan ................... 60-134794

[51] Int. Cl.[4] .......................... A23L 1/304; A23B 7/00
[52] U.S. Cl. ..................... 426/322; 426/74; 426/615
[58] Field of Search ............. 426/321, 615, 74, 322, 426/323, 93, 102, 309, 629, 419, 506, 326

[56] References Cited
FOREIGN PATENT DOCUMENTS
46-28125   8/1971  Japan .
58-24504   2/1983  Japan .
58-27318   6/1983  Japan .
224479    11/1985  Japan ................... 426/321
57824     12/1985  Japan ................... 426/74
40757      2/1986  Japan ................... 426/74

Primary Examiner—Donald E. Czaja
Assistant Examiner—Carolyn Paden
Attorney, Agent, or Firm—Burns, Doane, Swecker & Mathis

[57] ABSTRACT

The present invention relates to a method enabling the freshness of vegetables to be easily maintained by increasing the germanium content of vegetables and is characterized by comprising the treatment of the surfaces and/or inner parts of vegetables with an organic or inorganic germanium compound by a suitable method. In this case, the organogermanium compound is, for example, carboxyethylgermanium sesquioxide, and the inorganic germanium compound is, for example, germanium dioxide. It is possible to treat vegetables with an organic or inorganic compound in the state of an aqueous solution and the methods available include one in which vegetables are impregnated or are sprayed with the aqueous solution so that the germanium compound acts on the surfaces of the vegetables; and another in which the aqueous solution is absorbed by the roots of the vegetables so that the germanium compound acts on their inner parts.

11 Claims, No Drawings

METHOD FOR MAINTAINING FRESHNESS OF VEGETABLES BY INCREASING GERMANIUM CONTENT

INDUSTRIAL FIELD OF THE INVENTION

The present invention relates to a method enabling the freshness of vegetables to be easily maintained by increasing the germanium content of vegetables.

PRIOR ART

Since freshness is one of the most important factors for vegetables circulating within a market when considered as goods, various inventions have so far been accomplished with the aim of enabling the freshness of vegetables to be maintained.

Namely, it is conventional to adapt such conditions as manner of storage, storage location, temperature and ventilation for vegetables being stored so that their freshness may be maintained. In fact, the above-described conditions are adapted in suitable combinations, for example, vegetables are stored in a cool and dark place with mud still adhered to them or stored in a cool place with a supply of water.

On the other hand, freshness of vegetables is sometimes maintained by employing a special means adapted to keep certain species of vegetables. For example, a method has been adapted for radish sprouts in which they are held in a sponge bed containing a solution for water culture in the form wherein they have been recently supplied to the market in large amounts.

However, of the above-described conventional methods, the former has the disadvantage that it is necessary to set above-described conditions or a combination thereof in correspondence with the requirements of the particular vegetables to be kept fresh and/or to maintain the conditions for a long period. For example, a large amount of energy is consumed only for keeping vegetables at a low temperature during the carriage of such vegetables as are kept fresh by such means. This disadvantage becomes a main problem relative to the carriage of vegetables which have to be kept fresh.

It is obvious that the latter of the above-described conventional methods has no general-purpose utility and thus cannot be adapted for use with all vegetables.

The present invention has been accomplished for the purpose of providing a method which is capable of maintaining the freshness of vegetables by a simple method and which has general-purpose utility without involving any of the problems of the prior arts described above.

DISCLOSURE OF THE INVENTION

The method of the present invention is characterized by comprising the treatment of the surfaces and/or inner parts of vegetables with an organic or inorganic germanium compound by a suitable method.

The present invention will be described in detail hereinafter.

The vegetables to be kept fresh by means of the present invention are not particularly limited, and thus may include radish sprouts, chives, honewort and shallots, and in particular, the present invention can be used for those vegetables which suffer an extreme lowering in freshness when transported by conventional methods.

The germanium compound which is allowed to act on the vegetables described above may be an organic or inorganic compound but it is preferable for the facilitation of application to select a water-soluble germanium compound and to prepare an aqueous solution thereof.

As the inorganic germanium compound, germanium dioxide GeO$_2$ which is easily available on the market may be exemplified and as the organogermanium compound, carboxyethylgermanium sesquioxide (GeCH$_2$CH$_2$COOH)$_2$O$_3$ which can be produced by the processes shown by the following reaction formulas may be exemplified:

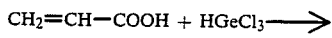

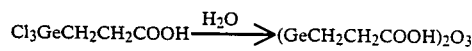

The element germanium (Ge) has been investigated for many years in the fields of physics and inorganic chemistry similar to silicon (Si) which in common with germanium is a homologue of carbon and has attracted much attention in other fields in recent years.

For example, certain items described below effectively used as Japanese and Chinese medicines and certain types of health food include a large amount of germanium and thus it has been proposed that germanium may be the main useful ingredient of the Japanese and Chinese medicine, etc.

Some of the organic derivatives of germanium exhibit remarkable pharmacologic activities. For example, it has been reported that carboxyethyl-germanium sesquioxide, described above, has significant antitumor properties while having no side-effects or toxicity, and this compound is expected to be useful as a pharmaceutical.

| Japanese and Chinese medicine | Germanium content (ppm) |
|---|---|
| Ginseng | 320 |
| Chinese garlic | 750 |
| Polypore | 2,000 |

Several attempts have been made to include such a germanium compound in plants; for example, Japanese Patent Laid-Open No. 118587/1978 discloses an invention which relates to a methiod for producing algae containing germanium, and describes a method, as an embodiment, in which chlorella and spirulina are used, but does not describe that the freshness of the vegetables can be maintained by increasing the germanium content.

The application if germanium compound to the vegetables can be divided broadly into two methods. In one of the methods, the vegetables are completely impregnated with an aqueous solution containing a germanium compound or are sprayed with the aqueous solution, so that the germanium compound acts on the surfaces of the vegetables; and in the other method, the aqueous solution containing the germanium compound is absorbed by the roots or the lower parts of the stalks of the vegetables, so that the germanium compound acts on the inner parts of the vegetables.

The above-described application methods may be simultaneously used, if required, and a suitable concentration of the germanium compound may be determined in accordance with type of the vegetables and the desired maintenance period of freshness. Seeds may be impregnated with the aqueous solution.

The vegetables treated by the above-described methods of the present invention were placed under the usual conditions in which food is stored and they were investigated by using the untreated vegetables as controls. It was confirmed by this investigation that the vegetables treated by the methods of the present invention contained an extremely large amount of germanium and maintained their freshness for a long period relative to the controls. Therefore, the present invention is particularly suitable for application to the production of vegetables in a production center which is far from the city where they will be consumed. In addition, the methods of the present invention require no specially-composed medium for vegetables which contain a large amount of germanium and which are kept fresh for long periods, and allows the employment of facilities which are conventionally used, without any need for modification, and thus the methods are particularly suitable for large scale culture. It will be obvious from the embodiments described below that when the methods of the present invention were employed, the yield and other properties showed no adverse effect, and the vegetables obtained displayed the same appearance and taste as conventional vegetables.

The mechanisms of these phenomena have not yet been clarified but are considered to be caused by the function of the germanium-oxygen bond.

PREFERRED EMBODIMENTS OF THE INVENTION

Embodiments of the present invention will be described hereinafter.

Embodiment 1

Investigation of germanium content (1) Radish sprout seeds were impregnated with an aqueous solution containing 30 ppm of germanium dioxide $GeO_2$ (referred to as IG hereinafter) for 2 hours, were then sown in foamed plastic sponge having a thickness of 2 cm in the usual manner, and the aqueous solution containing 30 ppm of IG was infiltrated into the sponge.

The seeds were germinated in a dark place at a temperature of 20° to 30° C. for 4 days, then outside at a temperature of 20° to 30° C. for 3 days, in accordance with the conventional method, and during this germination, the aqueous solution was sprayed on the seeds 3 times a day (1,000 ml of the aqueous solution was used).

The yield of the radish sprouts obtained in this manner was 750 g and their germanium content was as follows:
Root parts, 417.4 ppm
Leaf parts, 100.9 ppm (2) Radish sprout seeds were impregnated with an aqueous solution containing 100 ppm of carboxyethylgermanium sesquioxide $(GeCH_2CH_2COOH)_2O_3$ (referred to as OG hereinafter) for 2 hours, were then sown in foamed plastic sponge having a thickness of 2 cm by the conventional method, and the aqueous solution containing 100 ppm of OG was infiltrated into the sponge.

The seeds were germinated in a dark place at a temperature of 20° to 30° C. for 4 days, and outside at a temperature of 20° to 30° C. for 3 days, in accordance with the conventional method, and during this germination, the aqueous solution were sprayed on the seeds 3 times a day (1,000 ml of the aqueous solution was used).

The yield of the radish sprouts obtained in this manner was 770 g and their germanium content was as follows:
Root parts, 1,120.0 ppm
Leaf parts, 408.4 ppm

Embodiment 2

Freshness-maintaining effect of vegetables

1. Method

Groups of vegetables with roots such as radish sprouts, alfalfa, chives, honewort, and shallots and water-absorbing parsley which had been completely impregnated with an aqueous solution containing 10 ppm of IG or containing 10 ppm of OG for about 1 minute, and groups of the vegetables which had absorbed the IG or OG aqueous solution from their roots or the lower parts of their stalks for about 6 hours were stored in a cool, dark place (a refrigeration room), a room, and the atmosphere, in closed or opened plastic bags; and degrees of damage were observed with respect to control groups of vegetables which had absorbed only water for about 6 hours.

Tomatoes were also subjected to the same treatment, and were divided into the same groups for observation.

As the results of observation twice a day, the "degree of damage" was broadly classified into five steps depending on the degrees of discoloration, drying, and decomposition. However, since the degrees of damage of different vegetables differed from each other, criteria were determined as shown below, depending upon the types of vegetable.

| Damage degree | Criteria | | | | |
| --- | --- | --- | --- | --- | --- |
| | Radish sprouts Alfalfa | Chives | Honewort | Parsley | Shallots |
| − | Unchanged | Unchanged | Unchanged | Unchanged | Unchanged |
| + | Starting to discolor | Starting to droop | Starting to droop | Starting to droop (leaves becoming round) | Stalk starting to discolor |
| + + | About 20% discolored | Starting to dry up | About 20% drooping | About 20% drooping | Starting to dry up |
| + + + | About 40% discolored | About 20% dried up | About 40% drooping | Stalk starting to decompose | About 40% dried up |
| + + + + | 50% or more discolored, starting to droop | About 40% dried up | Starting to decompose | Drying-up in progress, stalk dividing | Complete drying up |
| + + + + + | Extensive decomposition | Some unusable | Leaves yellowed, extensive decomposition | Decomposition of main stalk | Unusable |

2. Experimental results (1) The results obtained for vegetables in closed plastic bags in a cool, dark place (a refrigeration room) are as follows:

[Radish sprouts]

| Day | 1 | 2 | 3 | 4 | 5 |
|---|---|---|---|---|---|
| Control | + | +++ | +++ | +++ | +++ |
| IG immersion for 1 min. | + | ++ | ++ | ++ | ++ |
| IG absorption for 6 hr. | − | + | + | + | + |
| OG immersion for 1 min. | + | ++ | ++ | ++ | ++ |
| OG absorption for 6 hr. | − | + | + | + | + |

[Alfalfa]

| Day | 1 | 2 | 3 | 4 | 5 |
|---|---|---|---|---|---|
| Control | + | +++ | +++ | +++ | +++ |
| IG immersion for 1 min. | + | ++ | ++ | ++ | ++ |
| IG absorption for 6 hr. | − | + | + | + | + |
| OG immersion for 1 min. | + | ++ | ++ | ++ | ++ |
| OG absorption for 6 hr. | − | + | + | + | + |

[Honewort]

| Day | 1 | 2 | 3 | 4 | 5 |
|---|---|---|---|---|---|
| Control | − | +++ | +++ | +++ | +++ |
| IG immersion for 1 min. | − | ++ | ++ | ++ | ++ |
| IG absorption for 6 hr. | − | + | + | + | + |
| OG immersion for 1 min. | − | + | ++ | ++ | ++ |
| OG absorption for 6 hr. | − | + | + | + | + |

[Parsley]

| Day | 1 | 2 | 3 | 4 | 5 |
|---|---|---|---|---|---|
| Control | − | − | + | ++ | +++ |
| IG immersion for 1 min. | − | − | + | + | ++ |
| IG absorption for 6 hr. | − | − | − | + | + |
| OG immersion for 1 min. | − | − | + | + | ++ |
| OG absorption for 6 hr. | − | − | − | − | + |

[Shallots]

| Day | 1 | 2 | 3 | 4 | 5 |
|---|---|---|---|---|---|
| Control | − | − | + | + | + |
| IG immersion for 1 min. | − | − | + | + | + |
| IG absorption for 6 hr. | − | − | − | − | + |
| OG immersion for 1 min. | − | − | + | + | + |
| OG absorption for 6 hr. | − | − | − | − | + |

(2) The results obtained for vegetables in closed plastic bags in a room were as follows:

[Radish sprouts]

| Day | 1 | 2 | 3 |
|---|---|---|---|
| Control | +++ | +++++ | +++++ |
| IG immersion for 1 min. | + | ++++ | +++++ |
| IG absorption for 6 hr. | − | +++ | ++++ |
| OG immersion for 1 min. | − | +++ | ++++ |
| OG absorption for 6 hr. | − | +++ | +++ |

[Alfalfa]

| Day | 1 | 2 | 3 |
|---|---|---|---|
| Control | +++ | +++++ | +++++ |
| IG immersion for 1 min. | + | ++++ | +++++ |
| IG absorption for 6 hr. | − | +++ | ++++ |
| OG immersion for 1 min. | + | +++ | ++++ |
| OG absorption for 6 hr. | − | +++ | +++ |

[Chives]

| Day | 1 | 2 | 3 | 4 | 5 |
|---|---|---|---|---|---|
| Control | − | + | ++ | +++ | ++++ |
| IG immersion for 1 min. | − | − | + | +++ | ++++ |
| IG absorption for 6 hr. | − | − | − | + | ++ |
| OG immersion for 1 min. | − | − | + | ++ | +++ |
| OG absorption for 6 hr. | − | − | − | + | ++ |

[Parsley]

| Day | 1 | 2 | 3 | 4 | 5 |
|---|---|---|---|---|---|
| Control | ++ | ++ | +++ | +++ | +++++ |
| IG immersion for 1 min. | + | ++ | ++ | +++ | +++ |
| IG absorption for 6 hr. | − | − | + | + | + |
| OG immersion for 1 min. | + | ++ | ++ | ++ | +++ |
| OG absorption for 6 hr. | − | − | + | + | + |

[Shallots]

| Day | 1 | 2 | 3 | 4 | 5 |
|---|---|---|---|---|---|
| Control | + | ++ | +++ | ++++ | +++++ |
| IG immersion for 1 min. | + | + | ++ | ++ | ++ |
| IG absorption for 6 hr. | − | + | + | + | + |
| OG immersion for 1 min. | + | + | ++ | ++ | ++ |
| OG absorption for 6 hr. | − | + | + | + | + |

(3) The results obtained for vegetables in opened plastic bags in a room were as follows:

[Radish sprouts]

| Day | 1 | 2 | 3 | 4 | 5 |
|---|---|---|---|---|---|
| Control | − | ++ | ++++ | ++++ | +++++ |
| IG immersion for 1 min. | − | + | +++ | ++++ | +++++ |
| IG absorption for 6 hr. | − | − | + | ++++ | +++++ |
| OG immersion for 1 min. | − | + | +++ | ++++ | +++++ |
| OG absorption for 6 hr. | − | − | + | ++++ | +++++ |

[Alfalfa]

| Day | 1 | 2 | 3 | 4 | 5 |
|---|---|---|---|---|---|
| Control | − | ++ | ++++ | ++++ | +++++ |
| IG immersion for 1 min. | − | + | +++ | ++++ | +++++ |
| IG absorption for 6 hr. | − | − | + | ++++ | +++++ |
| OG immersion for 1 min. | − | + | +++ | ++++ | +++++ |
| OG absorption for 6 hr. | − | − | + | ++++ | +++++ |

[Chives]

| Day | 1 | 2 | 3 | 4 | 5 |
|---|---|---|---|---|---|
| Control | − | + | ++ | +++ | +++ |
| IG immersion for 1 min. | − | − | + | ++ | ++ |
| IG absorption for 6 hr. | − | − | + | ++ | ++ |
| OG immersion for 1 min. | − | − | + | ++ | ++ |

-continued

[Chives]

| Day | 1 | 2 | 3 | 4 | 5 |
|---|---|---|---|---|---|
| OG absorption for 6 hr. | − | − | + | ++ | ++ |

[Honewort]

| Day | 1 | 2 | 3 | 4 | 5 |
|---|---|---|---|---|---|
| Control | − | + | ++ | +++ | ++++ |
| IG immersion for 1 min. | − | − | + | ++ | +++ |
| IG absorption for 6 hr. | − | − | + | ++ | +++ |
| OG immersion for 1 min. | − | − | + | ++ | +++ |
| OG absorption for 6 hr. | − | − | + | ++ | +++ |

[Parsley]

| Day | 1 | 2 | 3 | 4 | 5 |
|---|---|---|---|---|---|
| Control | − | ++ | +++ | +++ | +++++ |
| IG immersion for 1 min. | − | + | + | ++ | ++ |
| IG absorption for 6 hr. | − | − | − | − | + |
| OG immersion for 1 min. | − | + | + | + | ++ |
| OG absorption for 6 hr. | − | − | − | − | + |

[Shallots]

| Day | 1 | 2 | 3 | 4 | 5 |
|---|---|---|---|---|---|
| Control | − | + | +++ | ++++ | ++++ |
| IG immersion for 1 min. | − | + | ++ | +++ | ++++ |
| IG absorption for 6 hr. | − | + | + | ++ | ++++ |
| OG immersion for 1 min. | − | + | ++ | +++ | ++++ |
| OG absorption for 6 hr. | − | + | + | ++ | ++++ |

(4) The results obtained for vegetables allowed to stand in the atmosphere were as follows:

[Radish sprouts]

| Day | 1 | 2 | 3 | 4 | 5 |
|---|---|---|---|---|---|
| Control | − | ++ | +++ | ++++ | +++++ |
| IG immersion for 1 min. | − | + | ++ | +++ | +++ |
| IG absorption for 6 hr. | − | + | ++ | +++ | +++ |
| OG immersion for 1 min. | − | + | ++ | +++ | +++ |
| OG absorption for 6 hr. | − | + | ++ | +++ | +++ |

[Alfalfa]

| Day | 1 | 2 | 3 | 4 | 5 |
|---|---|---|---|---|---|
| Control | − | ++ | +++ | ++++ | +++++ |
| IG immersion for 1 min. | − | + | ++ | +++ | +++ |
| IG absorption for 6 hr. | − | + | ++ | +++ | +++ |
| OG immersion for 1 min. | − | + | ++ | +++ | +++ |
| OG absorption for 6 hr. | − | + | ++ | +++ | +++ |

[Chives]

| Day | 1 | 2 | 3 | 4 | 5 |
|---|---|---|---|---|---|
| Control | − | + | +++ | +++ | +++++ |
| IG immersion for 1 min. | − | + | ++ | +++ | ++++ |
| IG absorption for 6 hr. | − | + | ++ | ++ | +++ |
| OG immersion for 1 min. | − | + | ++ | +++ | ++++ |

-continued

[Chives]

| Day | 1 | 2 | 3 | 4 | 5 |
|---|---|---|---|---|---|
| OG absorption for 6 hr. | − | + | ++ | ++ | +++ |

[Honewort]

| Day | 1 | 2 | 3 | 4 | 5 |
|---|---|---|---|---|---|
| Control | − | ++ | ++++ | ++++ | +++++ |
| IG immersion for 1 min. | − | ++ | ++++ | ++++ | +++++ |
| IG absorption for 6 hr. | − | + | +++ | +++ | ++++ |
| OG immersion for 1 min. | − | ++ | ++++ | ++++ | +++++ |
| OG absorption for 6 hr. | − | + | +++ | +++ | ++++ |

[Parsley]

| Day | 1 | 2 | 3 | 4 | 5 |
|---|---|---|---|---|---|
| Control | + | +++ | ++++ | +++++ | +++++ |
| IG immersion for 1 min. | − | ++ | ++ | +++ | +++ |
| IG absorption for 6 hr. | − | + | + | ++ | ++ |
| OG immersion for 1 min. | − | + | ++ | +++ | +++ |
| OG absorption for 6 hr. | − | + | + | ++ | ++ |

[Shallots]

| Day | 1 | 2 | 3 | 4 | 5 |
|---|---|---|---|---|---|
| Control | − | + | ++ | +++ | ++++ |
| IG immersion for 1 min. | − | + | + | ++ | +++ |
| IG absorption for 6 hr. | − | + | + | ++ | +++ |
| OG immersion for 1 min. | − | + | + | ++ | +++ |
| OG absorption for 6 hr. | − | + | + | ++ | +++ |

TOMATOES

When tomatoes were allowed to stand in the atmosphere, the control group gathered mold after 8 days while tomatoes immersed for 6 hours manifested no mold even after 10 days through the inner parts were over-ripe.

INDUSTRIAL USABILITY

The present invention as described above has high utility as a method for maintaining the freshness of vegetables in the field of industry and is particularly suitable for application to the production of vegetables in a production center which is far from the city where they will be consumed.

We claim:

1. A method for maintaining the freshness of market transportable vegetables, said method comprising applying an effective amount of an organic or inorganic germanium compound to maintain freshness to substantially the entire surface of said market transportable vegetable.

2. The method according to claim 1 wherein said organic or inorganic germanium compound is in the form of an aqueous solution.

3. The method according to claim 1 wherein said organic germanium compound is carboxyethylgermanium sequioxide.

4. The method according to claim 1 wherein said inorganic germanium compound is germanium dioxide.

5. The method according to claim 1 wherein said vegetable is soaked in an aqueous solution of said organic or inorganic germanium compound.

6. The method according to claim 5 wherein said aqueous solution of an organic or inorganic germanium compound is sprayed onto the vegetable.

7. The method according to claim 6 wherein said organic germanium compound is carboxyethylgermanium sesquioxide.

8. The method according to claim 6 wherein said inorganic germanium compound is germanium dioxide.

9. A method for maintaining the freshness of market transportable vegetables having roots, said method comprising applying to said roots an aqueous solution of an organic or inorganic germanium compound and allowing said roots to absorb said compound.

10. The method according to claim 9 wherein said organic germanium compound is carboxyethylgermanium sesquioxide.

11. The method according to claim 9 wherein said inorganic germanium compound is germanium dioxide.

* * * * *